United States Patent [19]

Wakatsuki et al.

[11] Patent Number: 4,812,254

[45] Date of Patent: Mar. 14, 1989

[54] DETERGENT COMPOSITION

[75] Inventors: Junya Wakatsuki, Utsunomiya; Tomohiko Sano, Narashino; Tomihiro Kurosaki, Osaka, all of Japan

[73] Assignee: Kao Corporation, Tokyo, Japan

[21] Appl. No.: 155,291

[22] Filed: Feb. 12, 1988

[30] Foreign Application Priority Data

Feb. 20, 1987 [JP] Japan .................... 62-37226

[51] Int. Cl.$^4$ ............................. C11D 1/88
[52] U.S. Cl. ..................... 252/135; 252/174.16; 252/174.21; 252/DIG. 5; 252/DIG. 7; 252/DIG. 13
[58] Field of Search ............... 252/135, 174.21, 109, 252/174.16, 97, 528, DIG. 7, 547, DIG. 13, DIG. 5

[56] References Cited

U.S. PATENT DOCUMENTS 4,622,180 11/1986 Paltauf ........................ 260/389
4,714,571 12/1987 Tremblay ..................... 260/403

OTHER PUBLICATIONS

Blonder, E. et al. "Effects of Detergents and Choline--Containing Phospholipids on Human Spleen Glucocerebrosidase", Biochimica et Biophysica Acta, vol. 431 (1976), pp. 45-53.

Primary Examiner—Paul Lieberman
Assistant Examiner—Kathleen Markowski
Attorney, Agent, or Firm—Oblon, Fisher, Spivak, McClelland & Maier

[57] ABSTRACT

A detergent composition contains as an essential component a compound represented by the following general formula (I):

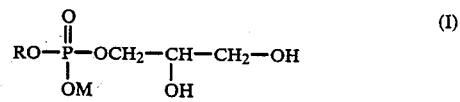

wherein R means

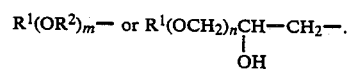

$R^1$ denotes a straight-chain or branched alkyl or alkenyl group or a substituted phenyl group. $R^2$ is an alkylene group having 2-3 carbon atoms, m is 0-30, and n stands for 0 or 1. M means a hydrogen atom or denotes an alkali metal, alkaline earth metal, zinc or aluminum atom, an ammonium ion, or an alkylamine or alkanolamine residuum thereby to indicate the formation of a salt of the compound of the general formula (I).

3 Claims, No Drawings

DETERGENT COMPOSITION

BACKGROUND OF THE INVENTION

(1) Field of the Invention

This invention relates to a novel detergent composition, more specifically, to a novel detergent composition having excellent detergency and foaming power, giving less irritation to the skin and hair and having moisturizing effects.

(2) Description of the Related Art

It has been known that phosphoric acid esters of organic hydroxy compounds are surfactants causing less irritation to the skin and having a high degree of safety for human bodies and are hence useful as base materials for detergent compositions and like products which are to be applied directly to human bodies. Reflecting the improved living standard, there is an ever-increasing demand for the development of perfume and cosmetic products and cosmetic base materials which have still higher safety and properties.

On the other hand, it is necessary to hold moisture suitably on the skin or hair in order to allow the skin or hair to give moisturized feeling to the touch. For this purpose, it is practised routinely to incorporate a moisturizer in detergents, shampoos, rinses and the like. Alkylene oxide addition products of glycerin, polyethylene glycol, urea, sorbitol or alcohols have conventionally been used as such moisturizers. As is envisaged from the foregoing, it has been known that a compound having one or more hydroxyl, polyether and/or like groups in its molecular structure shows moisturizing properties. When such a compound was added to a system which required rinsing with water, such as a detergent or shampoo, the compound was also washed away thereby failing to exhibit its effects. Accordingly, it has been desired to develop a moisturizer which even after being washed with water, can still remain in a suitable amount on the skin or hair and can retain suitable moisture on its surface.

SUMMARY OF THE INVENTION

With the foregoing in view, the present inventors have carried out an extensive investigation. As a result, it has been found that phosphoric esters having a specific structure have excellent foaming power and detergency, cause less irritation to the skin and hair, and even after being washed with water, remain in a suitable amount on the skin or the like and is hence effective in retaining moisture on its surface, leading to completion of the present invention.

In on aspect of this invention, there is thus provided a detergent composition which comprises a compound represented by the following general formula (I):

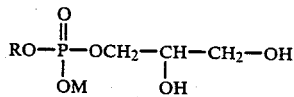
(I)

wherein R means

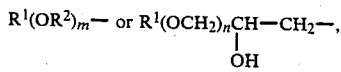

$R^1$ denotes a straight-chain or branched alkyl or alkenyl group having 1–36 carbon atoms, one or more hydrogen atoms of the alkyl or alkenyl group may optionally be substituted with the corresponding number of fluorine atoms, or a phenyl group substituted by a straight-chain or branched alkyl group having 1–15 carbon atoms, $R^2$ is an alkylene group having 2–3 carbon atoms, m is 0–30, n stands for 0 or 1, and M means a hydrogen atom or denotes an alkali metal, alkaline earth metal, zinc or aluminum atom, an ammonium ion, or an alkylamine or alkanolamine residuum thereby to indicate the formation of a salt of the compound of the general formula (I).

Detergent compositions according to this invention have excellent foaming power and detergency, cause less irritation to the skin or hair, and moreover, can remain in a suitable amount on the skin or the like even when treated subsequently, for example, washed with water, thereby exhibiting effects to retain suitable moisture on its surface. They are hence useful especially as face-washing cleansing formulations, shampoos, body shampoos and the like.

The above and other objects, features and advantages of the present invention will become apparent from the following description and the appended claim.

DETAILED DESCRIPTION OF THE INVENTION

In the compound which is represented by the formula (I) and is useful in the practice of this invention, as illustrative examples of the group R represented by $R^1(OR^2)_m-$, may be mentioned octyl, dodecyl, hexadecyl, octadecyl, tetracosyl, 2-ethylhexyl, 2-hexyldecyl, 2-octyldodecyl, 2-tetradecyloctadecyl, monomethyl-branched isostearyl, octenyl, dodecenyl, hexadecenyl, octadecenyl, triacontenyl, tridecafluorooctyl, heptadecafluorodecyl, heneicosafluorodecyl, pentacosafluorotetradecyl, nonacosafluorohexadecyl, 2-pentafluoroethylpentafluorohexyl, 2-tridecafluorohexyltridecafluorodecyl, 2-heptadecafluorooctylheptadecafluorododecyl, octylphenyl, nonylphenyl, polyoxyethylene(3) dodecyl ether, polyoxypropylene(3) decyl ether, polyoxyethylene(8) polyoxypropylene(3) dodecyl ether, polyoxyethylene(4) octadecenyl ether, polyoxyethylene(3) tridecafluorooctyl ether, polyoxyethylene(5) heptadecafluorodecyl ether, polyoxyethylene(3) heneicosafluorododecyl ether, polyoxyethylene(5) 2-tridecafluorohexyltridecafluorodecyl ether, polyoxyethylene(5) nonylphenyl ether, and polyoxypropylene(2) octylphenyl ether groups; as exemplary groups represented by

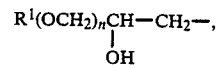

may be mentioned 2-hydroxydodecyl, 2-hydroxyhexadecyl, 2-hydroxytridecafluorononyl, 2-hydroxypentadecafluorodecyl, 2-hydroxyheptadecafluoroundecyl, 2-hydroxy-3-dodecyloxypropyl, 2-hydroxy-3-monomethyl-branched isostearyloxypropyl, 2-hydroxy-3-octadecenyloxypropyl, 2-hydroxy-3-heptadecafluorodecyloxypropyl and 2-hydroxy-3-(2-pentafluoroethylpentafluorohexyloxy)propyl groups.

Further, illustrative examples of the atom, ion or residuum represented by M may include, in addition to hydrogen atom, alkali metal atoms such as potassium and sodium atoms, alkaline earth metal atoms such as calcium and magnesium atoms, zinc atom, aluminum atom, ammonium ion, alkylamine residue such as triethylamine and tributylamine, and alkanolamine residue such as triethanolamine residuum. Among these, alkaline earth metal atoms such as calcium and magnesium atoms can suitably remain, in particular, on the skin or the like to effectively show moisturizing properties as an effect of the present invention. Compounds of this invention, in each of which M stands for an alkali metal atom or the like, have a low Kraft point, high detergency and strong foaming power. They do not impair at all the action of other detergent bases or the like and may themselves be used as detergents. When washed with tap water subsequent to their use, they undergo salt interchange with calcium ions or the like contained in the tap water so that their calcium salts or the like are formed.

The proportion of the compound of the formula (I) to be incorporated in the detergent composition according to this invention may vary depending on the form of the detergent composition, the kind of R and the kind of salt. In the case of liquid detergents for example, the proportion may generally range from 2 to 50 wt. % (will hereinafter be described merely as "%"), specifically, about 5-40% for compounds in which R is dodecyl and M is sodium atom, about 5-50% for compounds in which R is dodecyl and M is triethanolamine residuum, and about 5-20% for compounds in which R is tetradecyl and M is potassium atom. In the case of paste-like detergents, the proportion may generally range from 5 to 60%, specifically, about 20-50% for compounds in which R is decyl and M is sodium atom, about 10-30% for compounds in which R is dodecyl and M is potassium atom, and about 10-40% for compounds in which R is tetradecyl and M is triethanolamine residuum. In the case of solid detergents, the proportion may generally range from 10-90%, specifically, about 20-80% for compounds in which R is tetradecyl and M is sodium atom and about 30-80% for compounds in which R is dodecyl and M is potassium atom.

In addition to the compound of the above formula (I), the detergent composition of this invention may also contain an anionic surfactant, amphoteric surfactant, cationic surfactant or non-ionic surfactant which has been used widely as an active detergent ingredient.

The following compounds may be mentioned by way of example as usable anionic surfactants.

(1) Straight-chain or branched alkylbenzenesulfonates containing an alkyl group which has 8-16 carbon atoms on average.

(2) Polyoxyalkylene alkyl sulfate salts having a straight-chain or branched alkyl group of 8-20 carbon atoms on average and containing 0.5-12 moles of ethylene oxide and/or propylene oxide added per molecule.

(3) Alkyl sulfates having an alkyl group of 8-20 carbon atoms on average.

(4) Olefin sulfonates having 8-20 carbon atoms on average per molecule.

(5) Alkane sulfonates having 8-20 carbon atoms on average per molecule.

(6) Alkyl ethoxycarboxylates having an alkyl group of 8-20 carbon atoms on average and containing 0.5-12 moles of ethylene oxide added on average per molecule.

(7) Succinic acid derivatives represented by

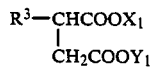

wherein $R^3$ means an alkyl or alkenyl group of 6-20 carbon atoms, and $X_1$ and $Y_1$ denote individually an ion.

As exemplary counter ions for these anionic surfactants, may be mentioned alkali metal ions such as sodium and potassium ions, alkaline earth metal ions such as magnesium ion, ammonium ion, and alkanolamine residua containing 1-3 alkanol groups of 2 or 3 carbon atoms (e.g., monoethanolamine residuum, diethanolamine residuum, teiethanolamine residuum, triisopropanolamine residuum, etc.).

Among these anionic surfactants mentioned above by way of example, particularly preferred are straight-chain or branched alkyl sulfates having 10-16 carbon atoms on average, polyoxyethylene alkyl sulfates (average mole number added: 0.5-8) in which the alkyl group has 8-20 carbon atoms on average, and olefin sulfonates having 10-16 carbon atoms on average.

Illustrative examples of the cationic surfactant may include quaternary ammonium salts represented by the following formula:

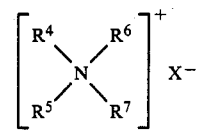

wherein one or two of $R^4$, $R^5$, $R^6$ and $R^7$ mean individually a straight-chain or branched long alkyl or hydroxyalkyl group having 8-20 carbon atoms and the remainders denote individually an alkyl group having 1-3 carbon atoms, hydroxyalkyl group or benzyl group, and X stands for a halogen atom or an alkyl sulfate group having 1-2 carbon atoms.

Of these, preferred are distearyl dimethyl ammonium chloride, stearyl trimethyl ammonium methosulfate, stearyl trimethyl ammonium chloride, stearyl dimethyl benzyl ammonium chloride, lauryl diethyl benzyl ammonium chloride, lauryl trimethyl ammonium bromide, distearyl methyl hydroxymethyl ammonium chloride, cetyl trimethyl ammonium chloride, etc.

The following compounds may be mentioned by way of example as preferred non-ionic surfactants.

(1) polyoxyethylene alkyl or alkenyl ethers having a primary or secondary alkyl or alkenyl group of 8-20 carbon atoms on average and added with 3-20 mole of ethylene oxide.

(2) Polyoxyethylene alkylphenyl ethers having an alkyl group of 8-12 carbon atoms on average and added with 3-20 moles of ethylene oxide.

(3) Higher fatty acid alkanolamides represented by the following formula or their alkylene oxide addition products:

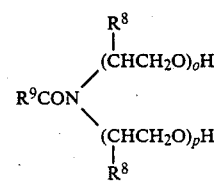

wherein $R^8$ means H or $CH_3$, $R^9$ denotes an alkyl or alkenyl group having 10-20 carbon atoms, o stands for an integer of 1-3, and p is an integer of 0-3.

The following compounds may be mentioned by way of example as preferred amphoteric surfactants.

(1) Alkylamine oxides represented by the following formula:

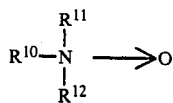

wherein $R^{10}$ is an alkyl or alkenyl group having 10-20 carbon atoms, and $R^{11}$ and $R^{12}$ denote individually an alkyl group having 1-3 carbon atoms and may be the same or different. Of these, preferred are those in which $R^{10}$ has 12-16 carbon atoms and $R^{11}$ and $R^{12}$ are individually a methyl group.

(2) Phosphoric esters represented by the following formula (II) or (III):

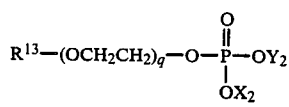

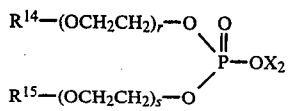

wherein $R^{13}$, $R^{14}$ $R^{15}$ mean individually a saturated or unsaturated hydrocarbon group having 8-18 carbon atoms, $X_2$ and $Y_2$ denote individually a hydrogen atom, or an alkali metal atom, ammonium ion or alkanolamine residuum having a hydroxyalkyl group of 2 or 3 carbon atoms thereby to indicate the formation of salts of the phosphoric esters of the formula (II) or (III), and q, r and s stand independently for a number of 0-10.

Among the above-mentioned surfactants of the phosphoric ester type, those added with 0-3 moles of ethylene oxide are preferred, with those added with no ethylene oxide and having an alkyl group of 12-14 carbon atoms being particularly preferred. As preferred specific examples, may be mentioned sodium mono- or dilauryl phosphate, potassium mono- or dilauryl phosphate, mono- or dilauryl phosphate diethanolamine, mono- or dilauryl phosphate triethanolamine, sodium mono- or dimyristyl phosphate, potassium mono- or dimyristyl phosphate, mono- or dimyristyl phosphate diethanolamine, mono- or dimyristyl phosphate triethanolamine, etc. Of these phosphoric ester surfactants, it is preferred to use as a mixture a compound of the formula (II) and a compound of the formula (III) at a weight ratio of 10:0-5:5, especially, 10:0-7:3.

(3) Quaternary ammonium salts represented by the following formula:

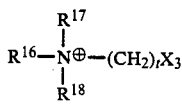

wherein $R^{16}$ means an alkyl or alkenyl group having 10-20 carbon atoms, $R^{17}$ and $R^{18}$ denote individually an alkyl group having 1-4 carbon atoms, t stands for an integer of 1-3, and $X_3$ means $-COO^{\ominus}$ or $-SO_3^{\ominus}$.

Of these, preferred are those in which $R^{16}$ has 12-16 carbon atoms, $R^{17}$ and $R^{18}$ are individually a methyl group, and t stands for 3.

(4) Imidazoline type compounds represented by the following formula:

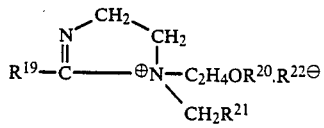

wherein $R^{19}$ means a fatty acid group having 10-20 carbon atoms, $R^{20}$ denotes a hydrogen or sodium atom or $CH_2COOR^{23}$ ($R^{23}$: H, Na or organic base residuum), $R^{21}$ is $COOR^{23}$, $CH_2COOR^{23}$ or

($R^{23}$: as defined above), and $R^{22\ominus}$ means a hydroxyl anion, inorganic anion, anionic surface-active sulfate or sulfated derivative.

These surfactants may be added to an extent not impairing the effects of the compound of the formula (I) useful in the practice of this invention, usually, in a range of 0.01-98%. Further, one or more of perfume bases, pigments, moisture conditioners, antiseptics, antioxidants and/or thickeners as well as one or more of medicinally-effective ingredients such as antidandruff agents, disinfectants, antiphlogistics and/or vitamins may also be added as needed.

Having generally described the invention, a more complete understanding can be obtained by reference to certain specific examples, which are provided herein for purposes of illustration only and are not intended to be limiting unless otherwise specified.

EXAMPLES

This invention will hereinafter be described by the following Examples.

EXAMPLE 1

(i) Placed in a reactor was 20.0 g (0.073 mole) of monododecyl phosphate of 97% purity, followed by an addition of 75.0 ml of a 1N aqueous solution of sodium hydroxide. The contents were stirred and heated to 70° C., thereby forming a homogeneous mixture. At that time, the acid value (the number of milligrams of KOH necessary to neutralize 1 g of a sample; the same definition will be applied hereinafter) of the reaction system was 42.9. While maintaining the reaction system at 70°-80° C., 24.0 g of glycidol was the added gradually and the resultant mixture was stirred at the same temperature for 6 hours. At that time, the acid value of the reaction system had been reduced practically to 0, thereby indicating the completion of the reaction. The reaction mixture was thereafter poured into 1,000 g of acetone. The resultant mixture was left over at 5° C. under cooling, so that the reaction product was crystallized. One day later, crystals precipitated were collected by filtration and then washed with acetone to obtain 18.3 g of white crystals of sodium dodecyl 2,3-dihydroxypropylphosphate [in the formula (I), $R=C_{12}H_{25}$ and $M=Na$].

(ii) The foaming power (by the reversal stirring testing method*) and the Kraft point of the above-obtained sodium dodecyl 2,3-dihydroxypropylphosphate were measured. Results will be shown subsequently in Table 1. It will be understood that compared with the corresponding sodium dodecyl phosphate as a comparative example, the foaming power is substantially the same but the Kraft point is significantly lower.

* Conditions for the reversal stirring testing:
Temperature: 40° C.
Revolutionary speed: 1,000 rpm
Stirring time: 30 seconds (revered every 5 seconds)
Measured after being left over for 10 seconds.

TABLE 1

|  | Foaming (foam volume, ml) | Kraft point (°C.) |
| --- | --- | --- |
| Monosodium dodecyl phosphate | 260 | 32 |
| Disodium dodecyl phosphate | 230 | 20 |
| Sodium dodecyl 2,3-dihydroxy-propylphosphate | 240 | <0 |

(iii) The moisturizing ability of the compound of this invention was confirmed by the following experimental method.

[Experimental method]

Skins, which had been treated with acetone and ether, were treated separately with a 5% aqueous solution of the invention compound (sodium dodecyl 2,3-dihydroxypropylphosphate), a 5% aqueous solution of monosodium dodecylphosphate and water and were then washed with hard water. The conductance of each skin was thereafter measured periodically. Conductance data measured upon an elapsed time of 120 minutes after the treatment will be shown subsequently in Table 2. It will be appreciated that the skin treated with the invention compound had a high conductance and moisture was retained when treated with the invention compound.

TABLE 2

|  | Conductance upon an elapsed time of 120 minutes |
| --- | --- |
| Skin treated with the invention compound, sodium dodecyl 2,3-dihydroxypropyl-phosphate | 22 (μυ) |
| Skin treated with monosodium dodecylphosphate | 10 (μυ) |
| Skin treated with water | 8 (μυ) |

(iv) By adding the invention compound, a detergent composition of Table 3 was prepared. The body shampoo had no irritation to the skin and after washing, the skin was refreshed without any clammy touch feeling and moreover, retained moisturized touch feeling even after the washing.

TABLE 3

| Formulation of Detergent Composition (Body Shampoo) | |
| --- | --- |
| Sodium dodecyl 2,3-dihydroxypropyl-phosphate | 25.0 wt. % |
| Lauryl phosphate triethanolamine | 5.0 |
| Lauryl dimethylamine oxide | 4.0 |
| Cationized cellulose | 0.1 |
| Glycerin | 5.0 |
| Sorbitol | 2.0 |
| Perfume base/antiseptic | q.v. |
| Purified water | balance |

EXAMPLE 2

In the same manner as in Example 1, sodium 2-hydroxy-3-dodecyloxypropyl-2,3-dihydroxypropyl-phosphate

[in the formula (1), R = $C_{12}H_{25}OCH_2\underset{\underset{OH}{|}}{C}HCH_2-$, M = Na]

was synthesized from mono(2-hydroxy-3-dodecyloxypropyl) phosphate.

By adding the above invention compound, a shampoo composition of Table 4 was prepared. The shampoo gave minute foams, imparted moisturized tough feeling to the hair and gave no irritation. It was hence preferred as a shampoo.

TABLE 4

| Shampoo | |
| --- | --- |
| Sodium 2-hydroxy-3-dodecyloxypropyl 2,3-dihydroxypropylphosphate | 15.0 wt. % |
| Coconut oil diethanolamide | 3.0 |
| Dodecyl dimethyl aminoacetate betaine | 3.0 |
| Disodium ethylenediamine tetraacetate | 0.1 |
| Citric acid | 0.1 |
| Purified water | balance |

We claim:

1. A detergent composition comprising 2–90 wt. % of a compound represented by the following formula (I):

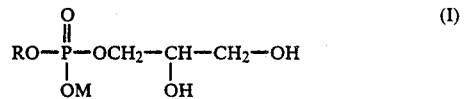

wherein R means

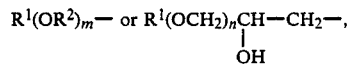

$R^1$ denotes a straight-chain or branched alkyl or alkenyl group having 1–36 carbon atoms, wherein one or more hydrogen atoms of the alkyl or alkenyl group may optionally be substituted with the corresponding number of fluorine atoms, or $R^1$ denotes a phenyl group substituted by a straight-chain or branched alkyl group having 1–15 carbon atoms, $R^2$ is an alkylene group having 2–3 carbon atoms, m is 0–30, n stands for 0 or 1, and M means a hydrogen atom or denotes an alkali metal, alkaline earth metal, zinc or aluminum atom, an ammonium ion, or an alkylamine or alkanolamine residuum thereby to indicate the formation of a salt of the compound of the formula (I).

2. The composition according to claim 1 wherein $R^1$ is a straight-chain or branched alkyl or alkenyl group having 1–36 carbon atoms, wherein one or more hydrogen atoms of the alkyl or alkenyl group may optionally be substituted with the corresponding number of fluorine atoms.

3. The composition according to claim 1 wherein $R^1$ is a phenyl group substituted by a straight-chain or branched alkyl group having 1–15 carbon atoms.

* * * * *